United States Patent [19]

Yoshino et al.

[11] Patent Number: 5,742,962
[45] Date of Patent: Apr. 28, 1998

[54] ARMREST

[75] Inventors: Futoshi Yoshino, Aioi; Mitsuo Oe, Utsunomiya, both of Japan

[73] Assignee: Kabushiki Kaisha Toshiba, Kawasaki, Japan

[21] Appl. No.: 874,883

[22] Filed: Jun. 13, 1997

Related U.S. Application Data

[63] Continuation of Ser. No. 582,420, Jan. 3, 1996, abandoned.

[30] Foreign Application Priority Data

Jan. 19, 1995 [JP] Japan ................................ 7-006338

[51] Int. Cl.[6] .................................................. A47B 16/00
[52] U.S. Cl. .............................. 5/623; 5/624; 5/621; 5/600
[58] Field of Search ...................................... 5/600, 621, 623, 5/624; 108/9; 297/411.2, 411.32, 411.34

[56] References Cited

U.S. PATENT DOCUMENTS

| | | | |
|---|---|---|---|
| 1,500,524 | 7/1924 | Phillips | 297/411.34 |
| 2,269,918 | 1/1942 | Sill | 297/417 |
| 3,046,072 | 7/1962 | Douglass et al. | 5/623 |
| 3,807,799 | 4/1974 | Freedman | 297/417 |
| 4,040,665 | 8/1977 | Wallace et al. | 297/411.32 |
| 4,616,637 | 10/1986 | Caspari et al. | 5/623 |
| 4,698,837 | 10/1987 | Van Steenburg | 5/623 |
| 5,133,097 | 7/1992 | Pyles | 5/623 |

*Primary Examiner*—Steven N. Meyers
*Assistant Examiner*—Frederick Conley
*Attorney, Agent, or Firm*—Oblon, Spivak, McClelland, Maier & Neustadt, P.C.

[57] ABSTRACT

The armrest of the present invention includes a first horizontal plate provided horizontally with a tabletop, a second horizontal plate jointed to the first horizontal plate by way of a hinge, this second horizontal plate forming a continuous horizontal surface along with the first horizontal plate when the hinge is opened, and the second horizontal plate being folded on the first horizontal plate so that a surface of the second horizontal plate meets a surface of the first horizontal plate when the hinge is closed, and a vertical plate provided vertically to the rear surface of the second horizontal plate. When the person sets a position in which he/she holds both arms down on the sides of the body, the hinge is opened, thus forming one horizontal plane, on which both arms can be laid down. When the person sets a position in which he/she folds both arms across the head, the hinge is closed, and the surface of the second horizontal plate is folded on the surface of the first horizontal plate. Thus, the rear surface of the second horizontal plate faces upward, and the vertical plate appears. The arms of the person which are held up above the head are supported by the vertical plates.

12 Claims, 4 Drawing Sheets

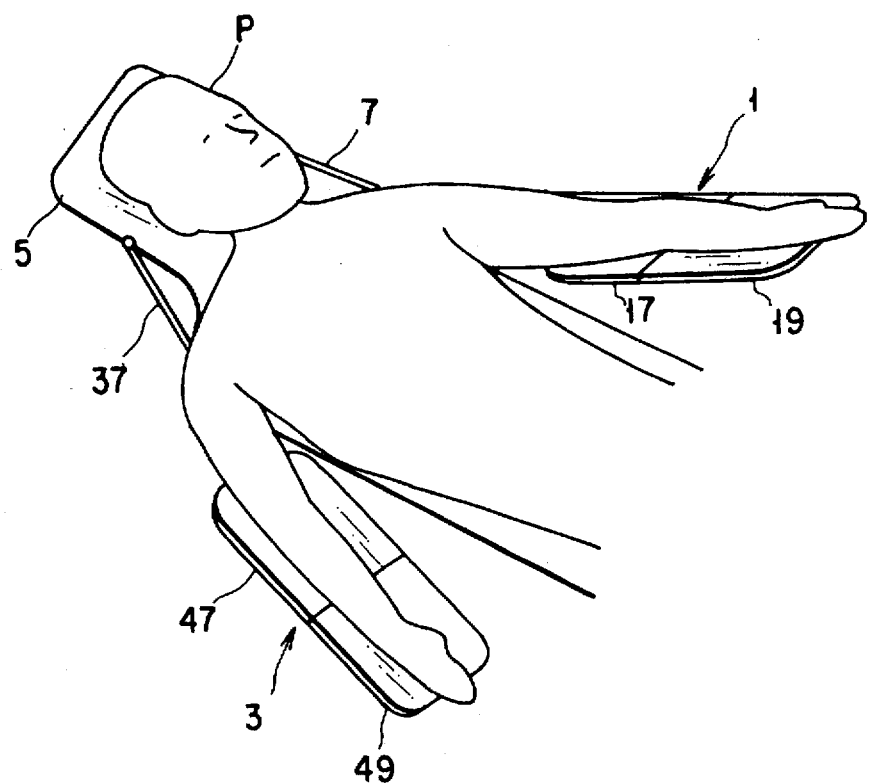
F I G. 6A
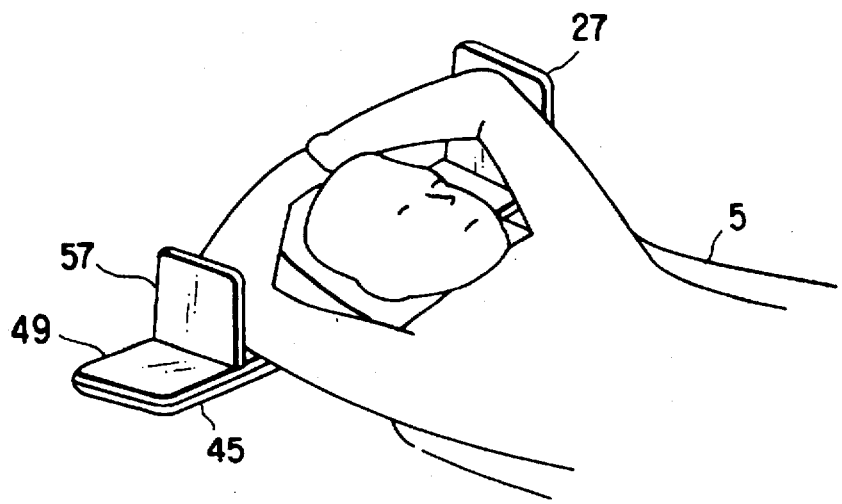
F I G. 6B

ARMREST

This application is a Continuation Ser. No. 08/582,420, filed on Jan. 3, 1996, now abandoned.

BACKGROUND OF THE INVENTION

1. Field of the Invention

The present invention relates to an armrest for a person to be examined, that is placed on a table top.

2. Description of the Related Art

The angiocardiography is a technique for photographing a flow of blood, a direction of extension of a blood vessel, a shape of a blood vessel, a movement of a valve, and the like by X-ray, with injection of a contrast medium having a high X-ray absorption rate, into an internal cavity of the heart or a blood vessel.

In a practice of the angiocardiography, a person to be examined, in many cases, is compelled to maintain a position in which he/she folds his/her arms across the top of his/her head during the time of the examination, so that the arms are not photographed by an X ray. However, for the person to be examined, it is a very hard to maintain such a position for a long time.

Conventionally, there is a table top provided with handgrips, to which a person to be examined can hold on to keep both hands above his/her head. With the handgrips, the strain on the person can be reduced.

However, some strain still exits even with the handgrips for the person who has to keep both hands above his/her head.

SUMMARY OF THE INVENTION

The object of the present invention is to provide an armrest which can deal with both positions in which the person holds down both hands on the sides of his/her body and in which the person holds up both hands above his/her head.

According to the present invention, there is provided an armrest comprising: a first horizontal plate provided horizontally with a tabletop; a second horizontal plate jointed to the first horizontal plate by means of a first hinge, the second horizontal plate forming a continuous horizontal surface along with the first horizontal plate when the hinge is opened, and the second horizontal plate being folded on the first horizontal plate so that a surface of the second horizontal plate meets a surface of the first horizontal plate when the first hinge is closed; and a vertical plate provided vertically to a rear surface of the second horizontal plate.

With the above structure, when the person holds his/her hands down on the sides of his/her body, the hinge is opened, and one horizontal surface is formed, on which the arms are laid down on the horizontal surface. In contrast, when the person holds his/her hands up above his/her head, the hinge is closed, and the surface of the second horizontal plate is folded on the surface of the first horizontal surface. In this manner, the rear surface of the second horizontal plate faces upward, and the vertical plate appears on the upper side. The hands held up above the person's head is pressed down by the vertical plate.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. 6A is a diagram showing how the armrest is used in a normal version; and

FIG. 6B is a diagram showing how the armrest is used in a flexed version.

DETAILED DESCRIPTION OF THE PREFERRED EMBODIMENT

An armrest according to an embodiment of the present invention will now be described with reference to accompanying drawings.

The position in which a person to be examined, is placed on a tabletop, and holds both arms down on the sides of the body, is defined as the "first position" (see FIG. 6A), whereas the position in which a person placed on a tabletop holds both hands above his/her head, is defined as the "second position" (see FIG. 6B).

Figure 1:
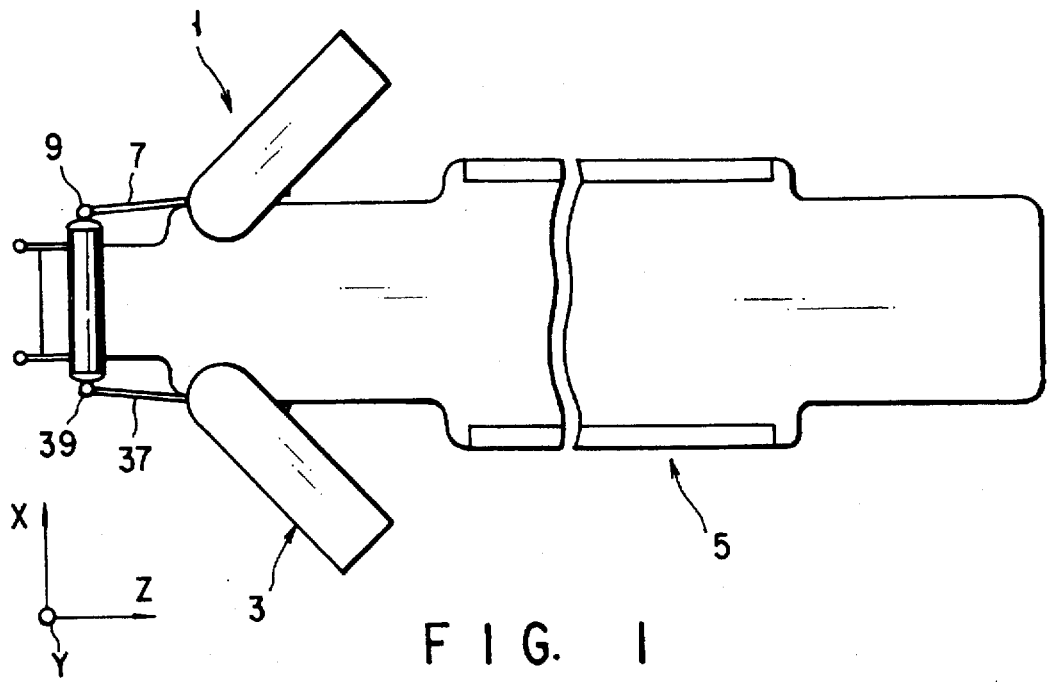
FIG. 1 is a plan view of an armrest according to an embodiment of the present invention, which is mounted to the table top.

As can be seen in FIG. 1, an armrest 1 for the left arm is provided on the left side of a tabletop 5 used for catheter, for supporting the left arm of the person placed on the tabletop 5. An armrest 3 for the right arm is provided on the right side of the tabletop 5, for supporting his/her left arm. The armrests 1 and 3 can be dismounted from the tabletop 5.

It should be noted that the longitudinal direction of the tabletop 5 is defined as the Z axis, the lateral direction thereof as the X axis, and the direction vertical to the surface of the tabletop 5, as the Y axis.

Figure 2A:
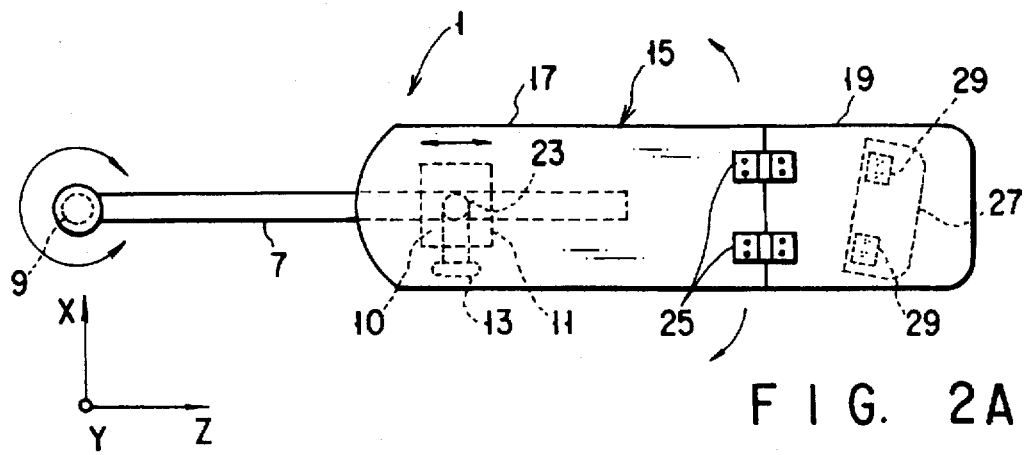
FIG. 2A is a plan view of an armrest for the left arm.
Figure 2B:
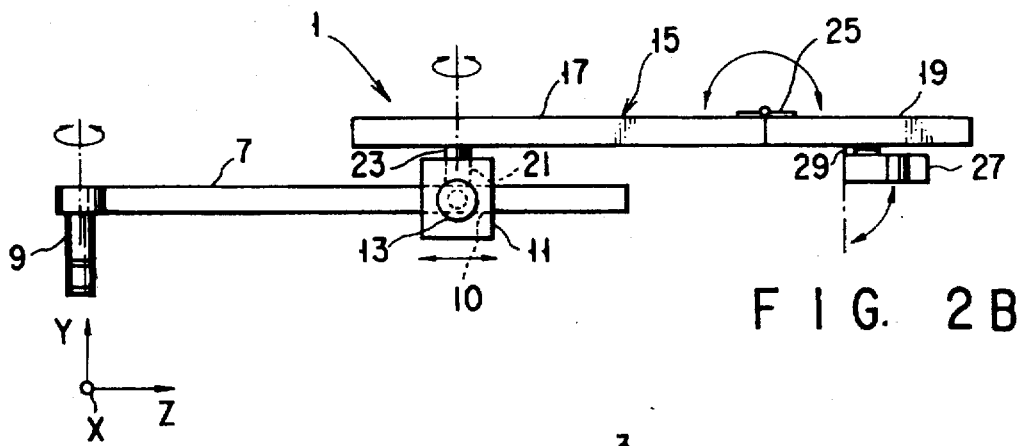
FIG. 2B is a side view of an armrest for the left arm.

FIG. 2A is a plan view of the armrest 1 for the left hand. FIG. 2B is a side view of the armrest 1. The tabletop 5 has, in its left side, a bearing hole made in parallel with the Y axis. Into this bearing hole, a rotation shaft 9 provided at right angles with a rod 7 on one end thereof is inserted. The rotation shaft 9 is freely rotatable in the bearing hole, and can be extracted from the bearing hole. A slider 11 is inserted into a through-hole 10 of the rod 7. When the knob of a fixation spring mechanism 13 is pressed, the slider 11 freely slides with respect to the rod 7. When the knob of the fixation spring mechanism 13 is released, the slider 11 is fixed on the rod 7.

A pin receiving hole 21 is formed in the slider 11 to be parallel with the Y axis. Into the pin receiving hole 21, a rotation pin 23 provided vertically on the rear surface of the horizontal plate 15, on which the person to be examined places his/her left arm, is inserted in such a manner that the rotation pin 23 cannot be pulled out but can be freely rotated.

The horizontal plate 15 is provided so that the surface thereof is flush with the surface of the tabletop 5. The horizontal plate 15 can freely rotate within an XZ plane, around each of the rotation axes of the rotation shaft 9 and the rotation pin 23, which are normal to each other. The distance between the horizontal plate 15 and the tabletop 5 can be varied. The horizontal plate 15 can be fixed at the position which is an arbitrary distance away from the tabletop 5.

The horizontal plate 15 is divided into a first horizontal plate 17 and a second horizontal plate 19. The first horizontal plate 17 and the second horizontal plate 19 are jointed to each other by means of a hinge 25. When the hinge 25 is opened, the surface of the second horizontal plate 19 is flushed with the surface of the first horizontal plate 17, forming one continuous plane. When the hinge 25 is closed, the surface of the second horizontal plate 19 is folded on the surface of the first horizontal plate 17.

A vertical plate 27 is set so as to be foldable, on the rear surface of the second horizontal plate 19 by means of a hinge 29. The vertical plate 27 is provided to be slanting with regard to the longitudinal direction of the horizontal plate 15. When the hinge 29 is opened, the vertical plate 27 is provided to be vertical to the second horizontal plate 19. When the hinge is closed, the vertical plate 27 is folded on the rear surface of the second horizontal plate 19.

A cushion material is adhered on the surface of each of the first and second horizontal plates 17 and 19. The cushion material is adhered also on the rear surface of the second horizontal plate 19 and on the side surface of the vertical plate 27.

Figure 3A:
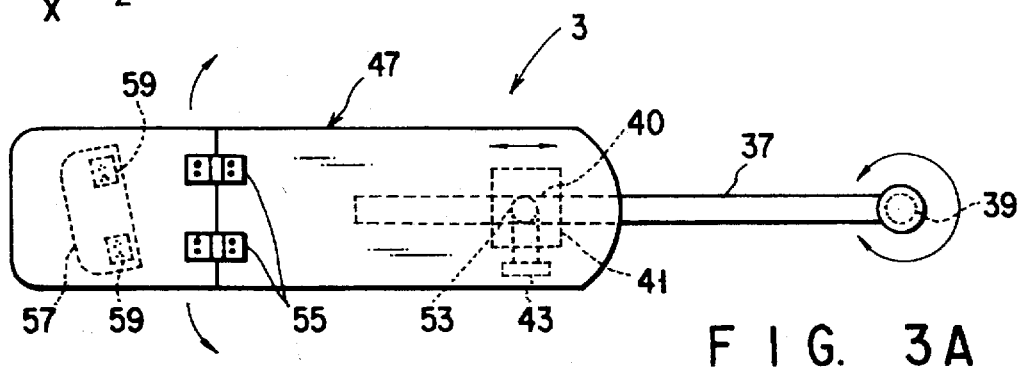
FIG. 3A is a plan view of an armrest for the right arm.
Figure 3B:
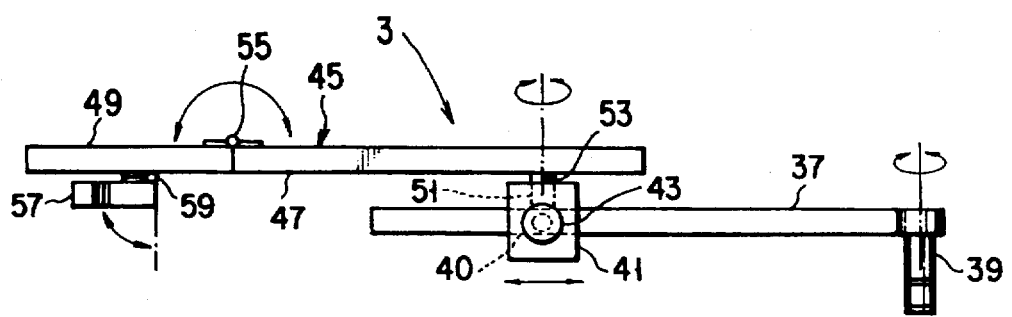
FIG. 3B is a side view of an armrest for the right arm.

FIG. 3A is a plan view of an armrest 3 for the right arm. FIG. 3B is a side view of the armrest 3. The tabletop 5 has, in its right side, a bearing hole made in parallel with the Y axis. Into this bearing hole, a rotation shaft 39 provided at right angles with a rod 37 on one end thereof is inserted. The rotation shaft 39 is freely rotatable in the bearing hole, and can be extracted from the bearing hole. A slider 41 is inserted into a through-hole 40 of the rod 37. When the knob of a fixation spring mechanism 43 is pressed, the slider 41 freely slides with respect to the rod 37. When the knob of the fixation spring mechanism 43 is released, the slider 41 is fixed on the rod 37.

A pin receiving hole 51 is formed in the slider 41 to be parallel with the Y axis. Into the pin receiving hole 51, a rotation pin 53 provided vertically on the rear surface of the horizontal plate 55, on which the person to be examined places his/her left arm, is inserted in such a manner that the rotation pin 53 cannot be pulled out but can be freely rotated.

The horizontal plate 45 is provided so that the surface thereof is flush with the surface of the tabletop 5. The horizontal plate 45 can freely rotate within an XZ plane, around each of the rotation axes of the rotation shaft 39 and the rotation pin 53, which are normal to each other. The distance between the horizontal plate 45 and the tabletop 5 can be varied. The horizontal plate 45 can be fixed at the position which is an arbitrary distance away from the tabletop 5.

The horizontal plate 45 is divided into a first horizontal plate 47 and a second horizontal plate 49. The first horizontal plate 47 and the second horizontal plate 49 are jointed to each other by means of a hinge 55. When the hinge 55 is opened, the surface of the second horizontal plate 49 is flushed with the surface of the first horizontal plate 47, forming one continuous plane. When the hinge 55 is closed, the surface of the second horizontal plate 49 is folded on the surface of the first horizontal plate 47.

A vertical plate 57 is set so as to be foldable, on the rear surface of the second horizontal plate 49 by means of a hinge 59. The vertical plate 57 is provided to be slanting with regard to the longitudinal direction of the horizontal plate 45. When the hinge 59 is opened, the vertical plate 57 is provided to be vertical to the second horizontal plate 49. When the hinge is closed, the vertical plate 57 is folded on the rear surface of the second horizontal plate 49.

A cushion material is adhered on the surface of each of the first and second horizontal plates 47 and 49. The cushion material is adhered also on the rear surface of the second horizontal plate 49 and on the side surface of the vertical plate 57.

FIG. 6A shows how the armrest is used in a normal situation. In this situation, a person P to be examined sets in the "first position" in which both arms are held down on the sides of the body. First, the operation with regard to the left arm will now be described. The hinge 25 is opened, and the first horizontal plate 17 and the second horizontal plate 19 make up the horizontal plate 15. The person P lies down on the tabletop 5, set in the "first position" facing upward, and places his/her left arm on the horizontal plate 15. Then, the person presses the knob of the fixation spring mechanism 13, and slides the horizontal plate 15 along the rod 7. At an appropriate position which corresponds to the length of the arm of the person P, the knob of the mechanism 13 is released, and thus the horizontal plate 15 is fixed to the rod 7 by means of the spring mechanism 13. The horizontal plate 15 can freely rotate around each of the rotation axes of the rotation shaft 9 and the rotation pin 23. With this structure, the person P can stretch his/her left arm towards a direction easy for him/her, or flex the left arm at an angle easy for him/her.

The operation with regard to the right arm is similar to that of the left arm, as will be described. The hinge 55 is opened, and the first horizontal plate 47 and the second horizontal plate 49 make up the horizontal plate 45. The person P lies down on the tabletop 5, set in the "first position" facing upward, and places his/her right arm on the horizontal plate 45. Then, the person presses the knob of the fixation spring mechanism 43, and slides the horizontal plate 45 along the rod 37. At an appropriate position which corresponds to the length of the arm of the person P, the knob of the mechanism 43 is released, and thus the horizontal plate 45 is fixed to the rod 37 by means of the spring mechanism 43. The horizontal plate 45 can freely rotate around each of the rotation axes of the rotation shaft 39 and the rotation pin 53. With this structure, the person P can stretch his/her right arm towards a direction easy for him/her, or flex the right arm at an angle easy for him/her.

When the person P lying down on the tabletop sets in the "second position" in which both hands are folded across the head, the armrest 1 is shifted from what is shown in FIG. 6A to FIG. 6B.

Figure 4A:
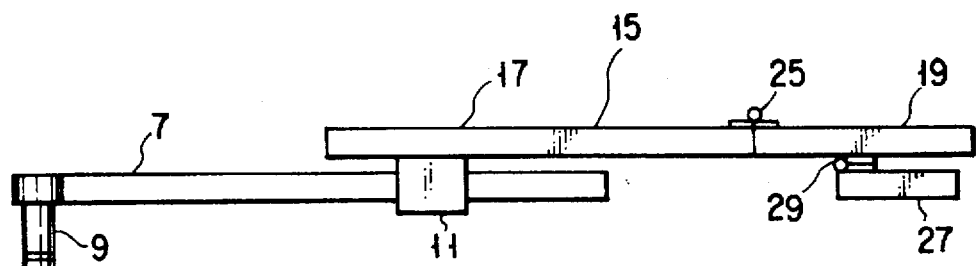
FIGS. 4A to 4D are side views illustrating a flexing process of the armrest for the left arm.
Figure 4B:
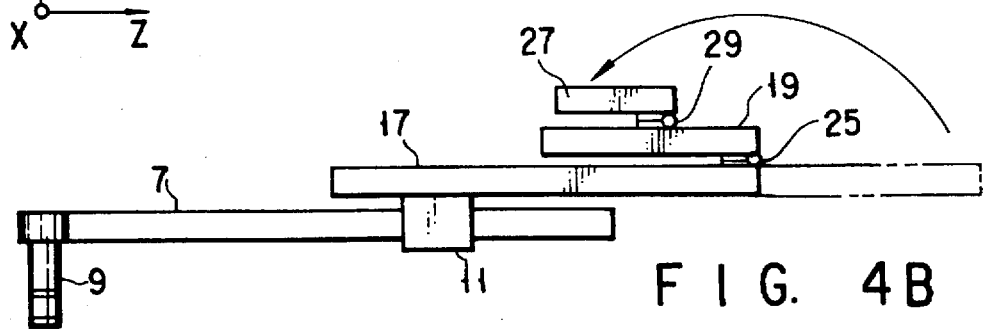
Figure 4C:
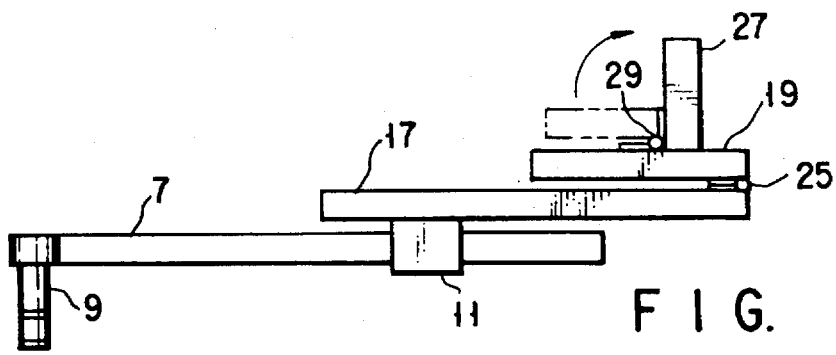
Figure 4D:
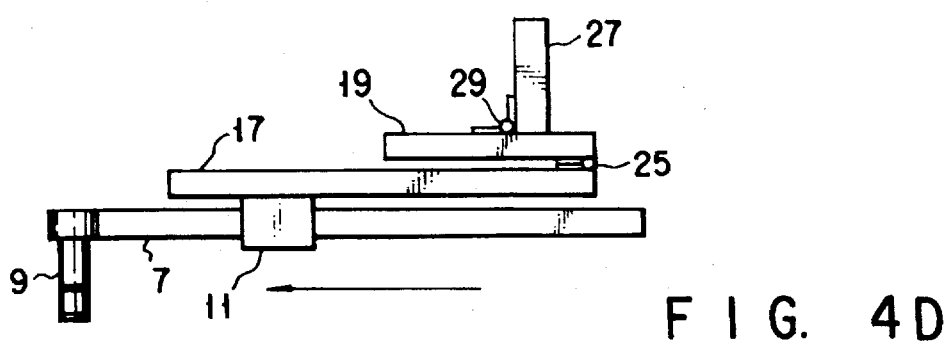

FIG. 4A to 4D are diagram illustrating the folding process of the armrest 1 for the left arm. As can be seen in FIGS. 4A and 4B, the hinge 25 is closed, and the second horizontal plate 19 is folded on the first horizontal plate 17. With this operation, the rear surface of the second horizontal plate 19 faces upwards, and the vertical plate 27 appears on the upper side. As can be seen in FIG. 4C, the hinge 29 is opened, and the vertical plate 27 is vertically stood up. The vertical plate 27 maintains its vertical state even if a force is applied from inside.

The person P lies down on the tabletop 5, set in the "second position" facing upward, and places his/her left arm on the surface of the first horizontal plate 17 and the rear surface of the second horizontal plate 19. At that time, the fixation spring mechanism 13 is released, and the horizontal plate 15 can slide along the rod 7. At an appropriate position where the plate stably supports the left elbow of the person P which has been bent around the head, the horizontal plate 15 is fixed to the rod 7 by means of the spring mechanism 13.

A shift of the armrest 3 for the right arm is similar to that of the left arm. The hinge 25 is closed, and the second horizontal plate 49 is folded on the first horizontal plate 47. With this operation, the rear surface of the second horizontal plate 49 faces upwards, and the vertical plate 57 appears on the upper side. Then, the hinge 59 is opened, and the vertical plate 57 is vertically stood up. The vertical plate 57 maintains its vertical state even if a force is applied from inside.

The person P lies down on the tabletop 5, set in the "second position" facing upward, and places his/her right arm on the surface of the first horizontal plate 47 and the rear surface of the second horizontal plate 49. At that time, the fixation spring mechanism 43 is released, and the horizontal plate 45 can slide along the rod 37. At an appropriate position where the plate stably supports the left elbow of the person P which has been bent around the head, the horizontal plate 45 is fixed to the rod 37 by means of the spring mechanism 43.

Both elbows of the person P are supported inward by the vertical plates 27 and 57. Therefore, it is not necessary for the person P to maintain the "second position" by himself/herself.

Figure 5:
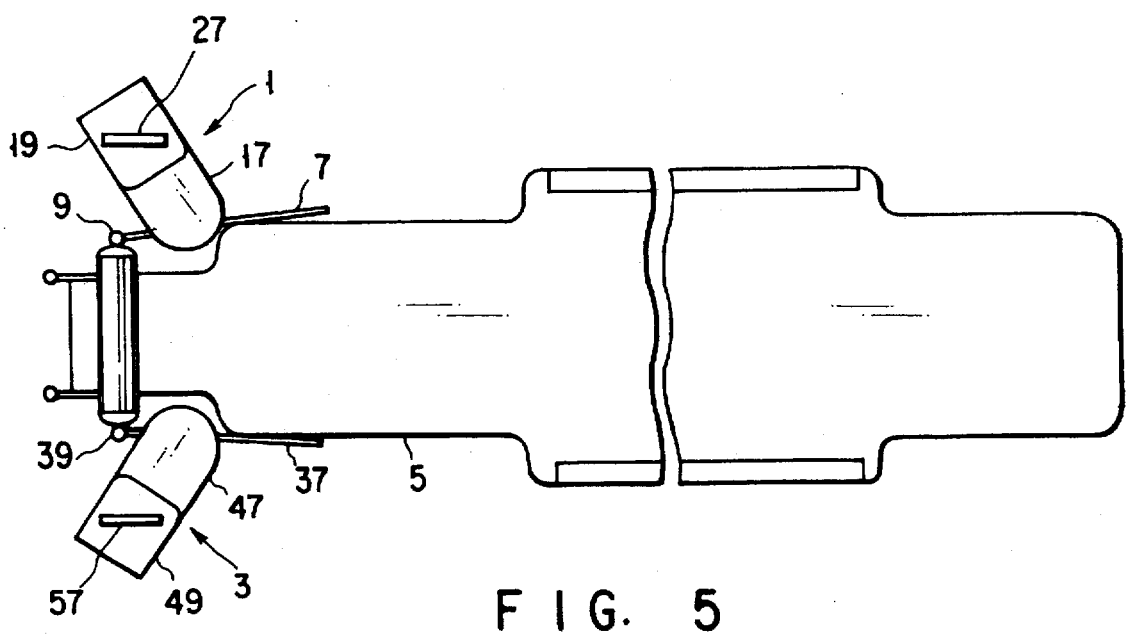
FIG. 5 is a plan view of the flexed armrest which is mounted on the table top.

FIG. 5 is a plan view showing the armrests 1 and 3 placed in different positions. The vertical plate 27 and 57 are situated to be slanting with the longitudinal directions of the horizontal plates 15 and 45, respectively. With this structure, the vertical plates 27 and 57 are located respectively in parallel with the elbows of the person P set in the "second position", so as to support the elbows of the person P not by point by plane. Therefore, the pain of the elbows can be eased.

As described above, the armrest of the present invention can deal with both the first and second positions, and can reduce the strain of a person who has to maintain each of these positions during an examination.

The present invention is not limited to the above-described embodiments, but can be remodeled into various versions.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An armrest assembly for an examination couch comprising:

a first horizontal member providing a horizontal surface;

a second horizontal member jointed to said first horizontal member by a first hinge, a surface of said second horizontal member forming a continuous horizontal surface along with the surface of said first horizontal member when said first hinge is in a first position, thereby an extended arm of a patient can be supported on said continuous horizontal surface, and said second horizontal member being folded on said first horizontal member when the first hinge is in a second position; and a vertical member having a vertical surface against a rear surface of said second horizontal member, said vertical member disappearing under said second horizontal member when said first hinge is in said first position, and appearing so as to steady a held-up arm of the patient when the first hinge is in said second position.

2. The armrest assembly according to claim 1, wherein said vertical member is provided hingedly to the rear surface of said second horizontal member by a second hinge.

3. The armrest assembly according to claim 1, further comprising:

a rod pivotally mounted on said couch; and a slider slidably provided with respect to said rod, and mounting said first horizontal member.

4. The armrest assembly according to claim 3, wherein said first horizontal member is provided pivotally on said slider.

5. The armrest assembly according to claim 3, further comprising:

a spring mechanism provided on said slider, said slider sliding with respect to said rod when a knob of said spring mechanism is pressed, said slider being fixed to said rod when the knob of said spring mechanism is released.

6. The armrest assembly according to claim 1, wherein said vertical plate is provided so as to be slanted with respect to a longitudinal direction of said first horizontal member.

7. An armrest assembly for an examination couch comprising:

a first member having a first horizontal surface;

a second member having a second surface;

a joint member for jointing said first member and said second member so that a position in which the first horizontal surface and said second surface face each other, and a position in which said first horizontal surface and said second surface are jointed to form a substantially flushed arm placement surface, can be selected;

a third member provided on said second member, which projects towards said first horizontal surface when said first horizontal surface and said second surface are positioned to face each other, thus suppressing a movement of an arm.

8. The armrest assembly according to claim 7, wherein said third member is provided foldably on a rear surface of said second member.

9. The armrest assembly according to claim 7, further comprising:

a rod pivotally mounted on said tabletop; and a slider slidably provided with respect to said rod, and mounting said first member.

10. The armrest according to claim 9, wherein said first member is provided pivotally on said slider.

11. The armrest assembly according to claim 9, further comprising:

a spring mechanism provided on said slider, said slider sliding with respect to said rod when a knob of said spring mechanism is pressed, said slider being fixed to said rod when the knob of said spring mechanism is released.

12. The armrest assembly according to claim 7, wherein said third member is provided so as to be slanted with respect to a longitudinal direction of said first member.

* * * * *